United States Patent [19]

Eilerman et al.

[11] Patent Number: 4,891,447

[45] Date of Patent: Jan. 2, 1990

[54] SANDALWOOD ODORANTS

[75] Inventors: Robert Eilerman, Merrick, N.Y.; Philip Christenson, Midland Park, N.J.; John Yurecko, Jr., Dayton, N.J.; Thomas Zebovitz, Colonia, N.J.

[73] Assignee: BASF K&F Corporation, Parsippany, N.J.

[21] Appl. No.: 285,782

[22] Filed: Dec. 16, 1988

[51] Int. Cl.$^4$ .......................................... C07C 47/198
[52] U.S. Cl. ..................................... 568/496; 568/448
[58] Field of Search ............... 568/672, 670, 448, 496, 568/497; 512/12, 5

[56] References Cited

U.S. PATENT DOCUMENTS

| 3,518,310 | 6/1970 | Lutz | 568/458 |
| 4,383,125 | 5/1983 | Harris et al. | 568/496 |
| 4,416,420 | 11/1983 | Harris et al. | 568/496 |
| 4,532,364 | 7/1985 | Fujioka et al. | 568/496 |

FOREIGN PATENT DOCUMENTS 2357753  5/1975  Fed. Rep. of Germany ...... 568/496

Primary Examiner—Werren B. Lone
Attorney, Agent, or Firm—Kenyon & Kenyon

[57] ABSTRACT

The present invention relates to novel substituted cyclohexanol compounds possessing a sandalwood aroma which are useful as fragrance materials. The invention also provides methods for synthesis thereof through a novel aldehyde intermediate. The compounds of the invention have the formula:

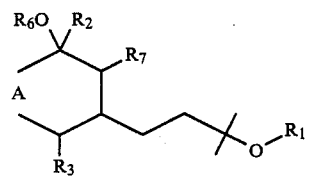

wherein A is

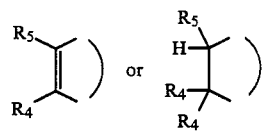

and wherein $R_1$ is methyl or ethyl, $R_2$–$R_7$ are independently hydrogen or methyl with the proviso that a maximum of two of the substituents $R_2$–$R_7$ are methyl, and $R_8$ is hydrogen, lower alkyl ($C_1$ to $C_5$) or acyl. The invention also provides fragrance compositions which utilize the compounds of the invention to impart a sandalwood aroma to perfume compositions, colognes and perfumed articles.

1 Claim, No Drawings

SANDALWOOD ODORANTS

FIELD OF THE INVENTION

This invention relates to novel components useful as fragrances, particularly those possessing a sandalwood aroma. The invention also provides an economical process for preparing these compounds.

BACKGROUND OF THE INVENTION

Certain chemicals possessing a sandalwood odor have enjoyed wide usage in fragrance compositions. The component of East Indian sandalwood oil (See E. J. Brunke and E. Klein, "Chemistry of Sandalwood Fragrance" in *Fragrance Chemistry*, E. T. Theimer, ed, Academic Press, p. 397,1982), obtained from *Santalum album* (Linn.), responsible for its sandalwood odor has been identified as (−)-β-santalol having the structure

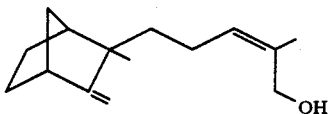

Other components of East Indian sandalwood oil that also possess the sandalwood odor, but not as intensely as (−)-β-santalol, are (+)-α-santalol and lanceal shown respectively below as structures

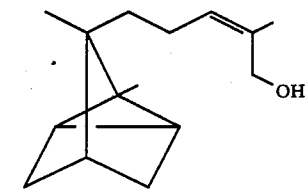

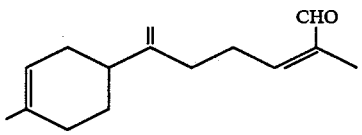

Various laboratory syntheses of these naturally occurring sandalwood chemicals have been reported (see U.S. Pat. No. 4,223,167). In addition, non-naturally occurring chemicals possessing the sandalwood odor have been synthesized. The dihydro-β-santalol (See Fanta and Erman, *J. Org. Chem.*, 37, 1624 (1972)) having the structure

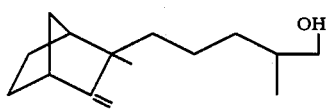

possesses a strong sandalwood note. The 3-desmethyl-β-santalols (See U.S. Pat. No. 3,673,261 issued 1972, and Fanta and Erman, 1972) having the structure

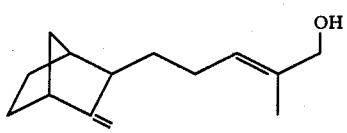

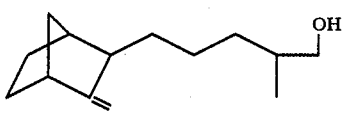

also possess a sandalwood note.

Certain monocyclic chemicals possessing the sandalwood odor have also been prepared in the laboratory. A chemical (See U.S. Pat. No. 4,046,716, issued 1977) having the structure

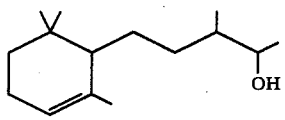

is reported as having a mild sandalwood odor.

The monocyclic alcohols (See U.S. Pat. No. 4,052,341, issued 1976, and Ger. Off. 1,922,391, issued 1970) shown respectively as structures

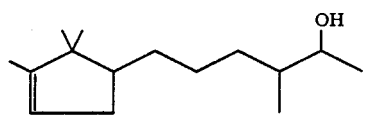

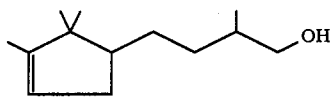

also possess the sandalwood aroma.

Certain acyclic chemicals possessing the sandalwood note have also been prepared in the laboratory. An example is the chemical (See Ger. Off. 2,244,199, issued 1973) having the structure

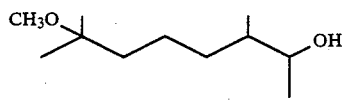

Certain non-naturally occurring substituted cyclohexanols possessing the sandalwood odor have been synthesized. U.S. Pat. No. 4,188,310, issued 1980, described the synthesis of a fragrance material having the structure

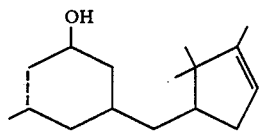

wherein the dashed line may be either a carbon-carbon single bond or a carbon-carbon double bond. A mixture of geometrical and optical isomers having the above structure is said to exhibit soft, warm woody notes rendering it useful as a fragrance material.

U.S. Pat. No. 4,104,203, issued 1978, describes another substituted cyclohexanol mixture having the structures

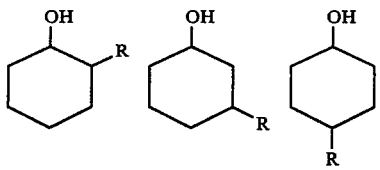

where R is

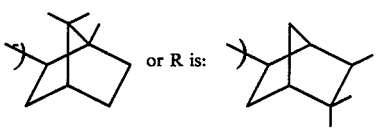

which were also reported to possess a strong sandalwood-type odor.

These known materials, however, have complex bicyclic structures and/or are difficult to synthesize. Therefore, it is an object of the invention to prepare a cyclohexanol compound that is devoid of a complex bicyclic structure yet has a sandalwood odor. Yet another object is to develop a compound that is synthetically easy to prepare.

SUMMARY OF THE INVENTION

These and other objects are achieved by the present invention which is directed to novel substituted cyclohexanol compounds possessing a strong sandalwood aroma. These compounds have the formula:

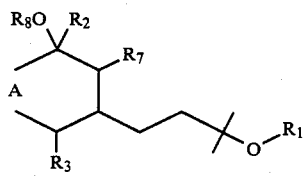 i wherein A is

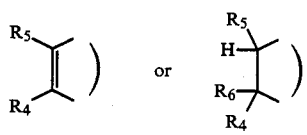

and where $R_1$ is methyl or ethyl, $R_2$–$R_7$ are independently hydrogen or methyl with the proviso that a maximum of two of the substituents $R_2$–$R_7$ are methyl, and $R_8$ is hydrogen, lower alkyl ($C_1$ to $C_5$) or acyl. It will be recognized that the compounds of the invention can exist in several stereoisomeric forms. The foregoing structural formulae are intended to embrace the individual stereoisomers, as well as mixtures of the various stereoisomers of the substituted cyclohexanols of this invention.

The present invention also provides efficient and economical processes for preparing these compounds.

Thus, for example, the compound having the structure

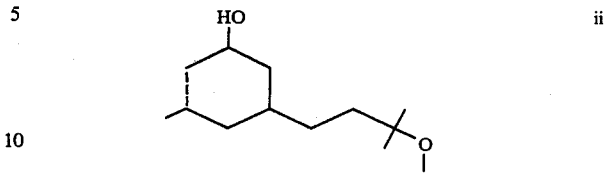 ii where the dotted line represents either a carbon-carbon single bond or a carbon-carbon double bond, may be prepared by condensation of an acetoacetic ester having the structure

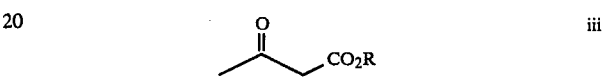 iii wherein R is a lower alkyl, and 4-methyl-4-methoxypentanal having the structure

 iv in the presence of a suitable base. The 4-methyl-4-methoxypentanal may be synthesized by hydroformylation of readily available 3-methoxy-3-methylbut-1-ene having the structure

 v

Condensation of the acetoacetic ester iii and 4-methyl-4-methoxypentanal iv forms a carboalkoxycyclohexenone having the structure

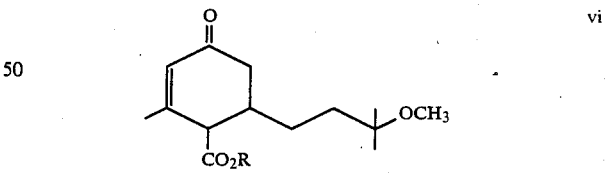 vi

Compound vi is then decarboxylated by conventional procedures such as treatment with alkali, to yield a compound having the structure

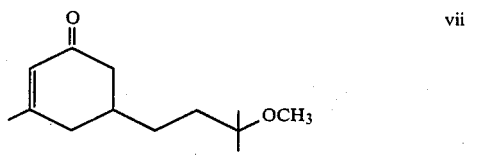 vii which upon reduction yields

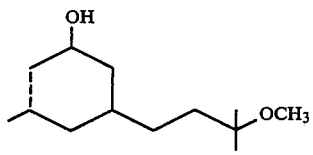

wherein the dashed line represents either a carbon-carbon single bond or a carbon-carbon double bond depending upon the conditions used for the reduction.

It has been found that the above compounds (formula i) and diastereoisomers either separately or as mixtures are useful as fragrance materials. Useful fragrance compositions have been prepared by incorporating these compounds or as admixtures.

DETAILED DESCRIPTION OF THE INVENTION

The novel substituted cyclohexanol compounds of the present invention possess a strong sandalwood aroma. They exhibit woody, musky nuances rendering them useful as fragrance materials. These compounds exhibit similar odor characteristics and may be used individually or as mixtures in fragrance applications. Geometrical and optical isomers of these compounds may be separated by techniques known to the art. However, such separations are not necessary, since these mixtures can be employed directly without further separations.

The following reaction schemes illustrate processes of the present invention for conveniently and efficiently preparing novel aldehyde intermediates, cyclohexanone intermediates and cyclohexanols and derivatives useful in the preparation of fragrance materials.

SCHEME I.
FORMATION OF ALDEHYDE INTERMEDIATE
Process 1:

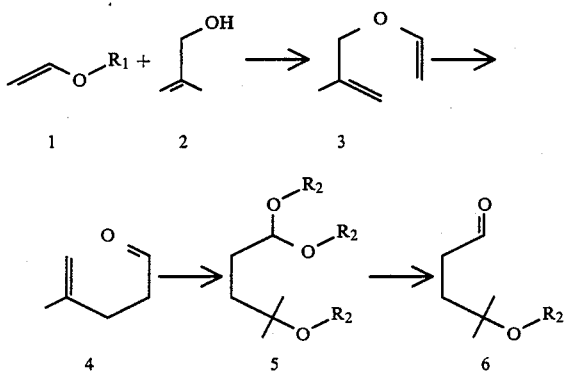

Process 2:

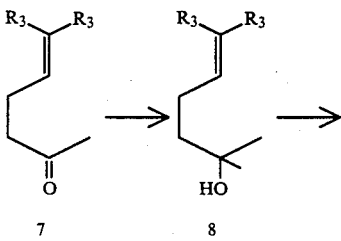

-continued
SCHEME I.
FORMATION OF ALDEHYDE INTERMEDIATE

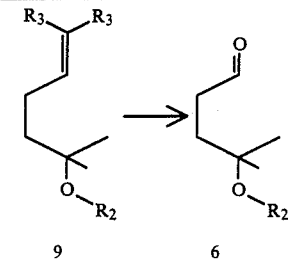

Process 3:

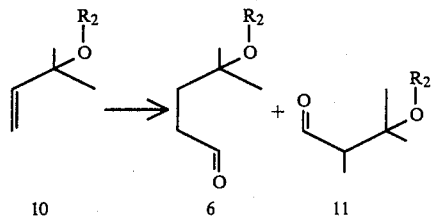

Process 4:

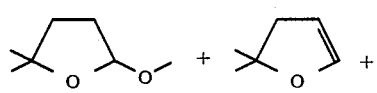

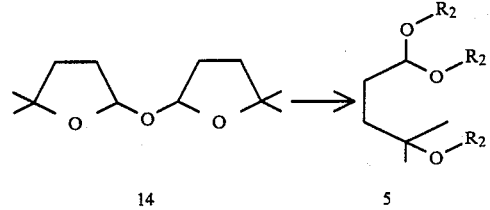

Four different processes are depicted in Scheme I for the formation of a novel aldehyde intermediate. In Process 1, 2-methylprop-2-en-1-ol (2) is heated in the range of 150° to 250° C. in the presence of a vinyl ether 1, wherein $R_1$ is ethyl and an acid catalyst such as phosphoric acid, toluenesulfonic acid or, preferably, mercuric acetate. This reaction is proposed to proceed through the intermediate enol ether 3 to generate the unsaturated aldehyde 4. The aldehyde 4 is then heated with methanol and an acid catalyst such as Dowex-50 acidic resin to provide the dimethylacetal compound 5 ($R_2$ is methyl). Hydrolysis of compound 5 using an acid catalyst such as formic acid, acetic acid, benzoic acid, hydrochloric acid, phosphoric acid or, preferably, oxalic acid, under aqueous conditions with heating provides the novel aldehyde 6. Compound 6 is a useful and novel intermediate for the synthesis of fragrance materials.

Process 2 in Scheme I depicts another method for producing the novel aldehyde compound 6. A starting compound 7, wherein $R_3$ is hydrogen or a lower alkyl group such as methyl, is treated with an organo-metallic reagent such as methylmagnesium iodide, methylmagnesium chloride or methyllithium under aprotic conditions to form, after an acidic workup, compound 8.

Compound 8 is etherified by treatment with a strong base such as sodium hydride, sodium metal, n-butyllithium or lithium hydride in an aprotic solvent such as THF or diethyl ether followed by addition of an alkylating agent such as dimethyl sulfate or methyl iodide to yield compound 9 where $R_2$ is methyl.

Ozonolysis of 9 is performed in the temperature range of −70° to −20° C. in a mixture of a chlorocarbon such as methylene chloride or dichloroethane and a low molecular weight alcohol solvent such as ethanol, 1-butanol, 2-propanol, 1-propanol or, preferably, methanol. The ratio of methylene chloride to methanol may range from 1:0 to 0:1, preferably 1:1. The intermediate ozonide is reduced with an appropriate reducing agent such as triphenylphosphine, sodium bisulfite or dimethyl sulfide, to form 6 ($R_2$ is methyl).

In Process 3 of Scheme I, 2-methoxy-2-methylbut-3-ene 10, prepared by the method of Tzeng and Weber (*J. Org. Chem.*, 46, 265 (1981)), incorporated herein by reference, from 2-methyl-3-buten-2-ol, is hydroformylated in a hydrocarbon solvent such as benzene, pentane, cyclohexane, heptane, octane, or, preferably, hexane, in the presence of a catalyst such as dicobaltoctacarbonyl or tris(triphenylphosphine)rhodium(I) chloride at temperatures of from 125° to 200° C. and pressures in the range of 1000 to 2000 psi to form a mixture of ethers 6 and 11 ($R_2$ is methyl).

In Process 4 of Scheme I the cyclic acetal 12 obtained by the procedure of U.S. Pat. No. 4,123,444, incorporated herein by reference, is converted into the ether acetal 5 by heating compound 12 in the presence of methanol, a mineral acid such as sulfuric acid, phosphoric acid, nitric acid, hydrochloric acid, hydrobromic acid or hydroiodic acid, a solid support such as Montmorillonite clay, DOWEX-50 ™ acidic resin, NAFION ™ or silica and an orthoformate ester such as trimethyl orthoformate for a time period of 1 hour to 3 days. Preferred conditions are 2 eq. of methanol, sulfuric acid catalyst, Montmorillonite clay and trimethyl orthoformate for 16 hours. Compound 5 is converted to aldehyde 6 using the method described in Process 1.

In addition, the side products of the hydroformylation of 3-methylbut-1-en-3-ol such as the dimeric ether 13 and enol ether 14 may also be subject to the above conditions to generate the acetal ether 5.

The aldehyde compound 6 ($R_2$ is methyl) is a unique and necessary intermediate toward the generation of novel and useful fragrance materials according to the invention.

Scheme II.
Formation of Cyclohexenone Intermediate

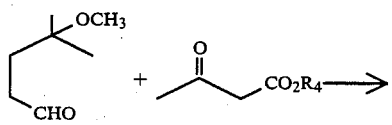

6                    14

-continued
Scheme II.
Formation of Cyclohexenone Intermediate

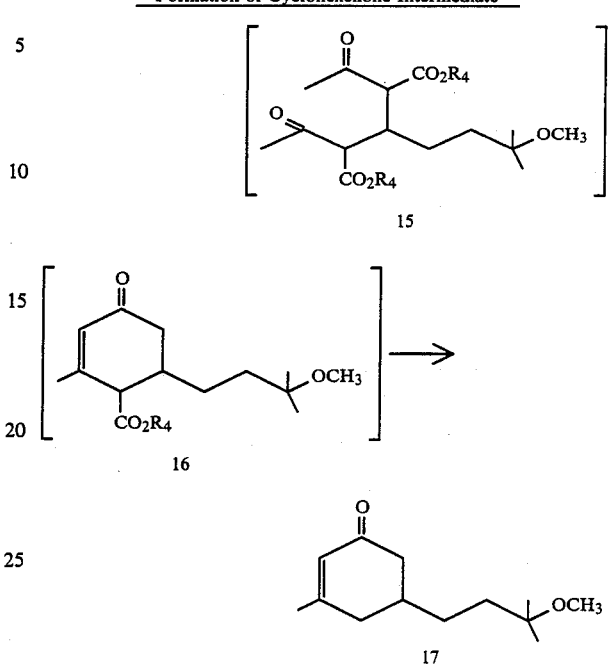

Scheme II depicts a pathway to the formation of intermediate cyclohexenones such as 17. Compound 17 represents the branch point for a variety of novel and useful fragrance materials. Aldehyde 6 is treated with an excess of the acetoacetate ester 14 ($R_4$ is a lower alkyl such as ethyl) in the presence of a suitable secondary amine base such as pyrrolidine, diethyl amine, morpholine or, preferably, piperidine, to form proposed unisolated intermediates 15 and 16 as per the procedure of U.S. Pat. No. 4,188,310. Compound 16 is decarbalkoxylated in the presence of a hydroxide base such as sodium hydroxide to yield cyclohexenone 17.

Scheme II can also be used to produce compounds of formula 17a:

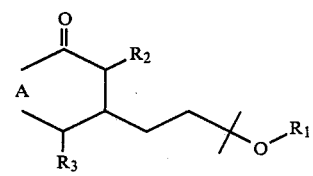

wherein A is

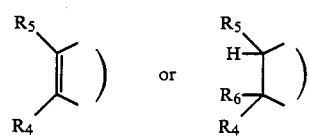

and where $R_1$ is methyl or ethyl, $R_2$–$R_6$ are independently hydrogen or methyl with the proviso that a maximum of two of the substituents $R_2$–$R_6$ are methyl. Compound 15 can be mildly condensed to form the corresponding cyclohexenone followed by protection of the ketone as a ketal and reduction of the carboxyl groups to methyl. In the same fashion, compound 16 can be converted to a ketal and the carboxyl group reduced to form a methyl.

Alternatively, compound 17 can be alkylated by condensing the enol base with methyl iodide. A mixture will result which can be separated to provide the desired products.

These compounds can be converted to compounds of formula i by the methods described in Scheme III.

yaluminum hydride, lithium borohydride, sodium bis(2-metyhoxyethoxy)-aluminum hydride, sodium cyanoborohydride or, preferably, lithium tri-sec-butylborohydride, provides the alcohol 20 as a mixture of four diastereoisomers. The depicted isomer 20 is the major component. This mixture is determined to possess strong, tenacious, sandalwoody, musky notes making it valuable as a fragrance material.

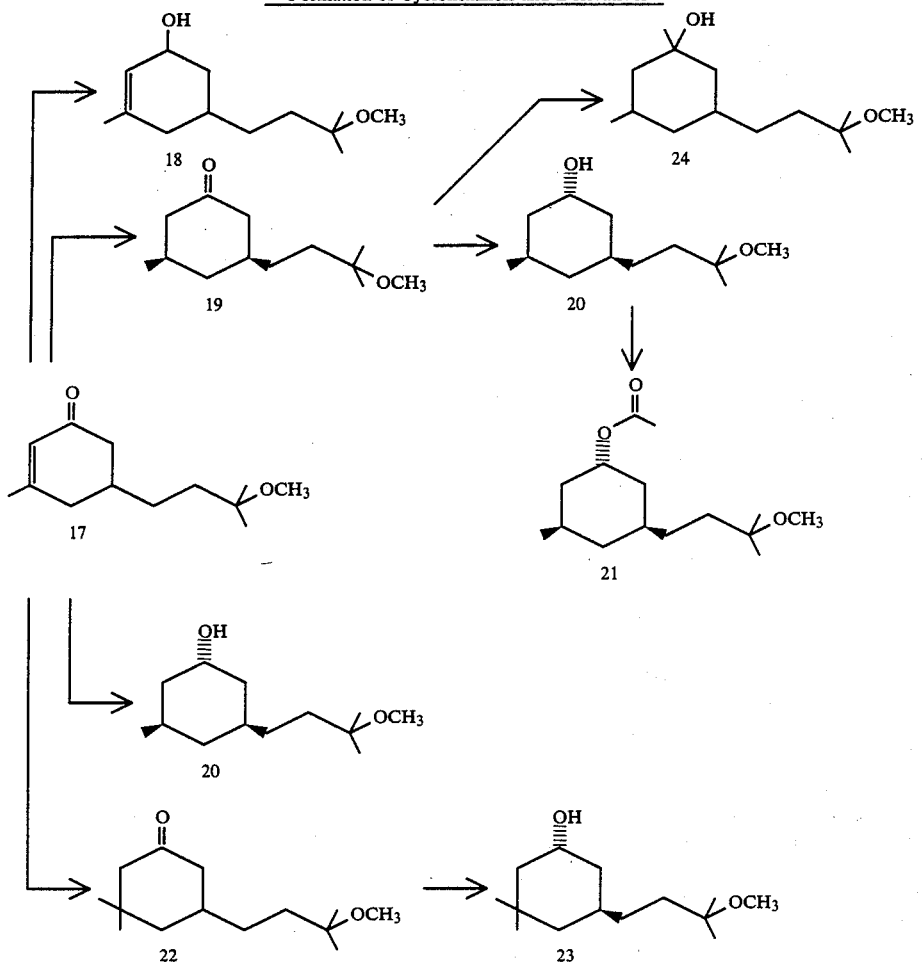

Scheme III.
Formation of Cyclohexanols and Derivatives

Scheme III depicts pathways to the formation of fragrance materials of this invention. Treatment of cyclohexenone 17 with a suitable reducing agent such as sodium borohydride, diisobutylaluminum hydride, lithium tri-tert-butoxyaluminum hydride, lithium borohydride, tri-sec-butylborohydride, sodium cyanoborohydride or, preferably, lithium aluminum hydride, generates the allylic alcohol 18 whose odor exhibits green, woody notes.

Hydrogenation of cyclohexenone 17 in the presence of a suitable catalyst such as Raney nickel, platinum oxide, iridium on carbon, rhodium on carbon or, preferably, 5% palladium on carbon provides the saturated ketone 19 as a mixture of two diastereoisomers. The depicted isomer is the major isomer in the palladium catalyzed reduction.

Reduction of ketone 19 with a suitable reducing agent such as lithium aluminum hydride, sodium borohydride, diisobutylaluminum hydride, lithium tri-tert-butox- A variety of methods are examined to effect the reduction of the unsaturated ketone 17 or saturated ketone 19 to alcohol 20. These are tabulated in Table I.

The alcohol 20 yields ester 21 in the presence of a suitable acylating agent such as acetic anhydride, acetyl chloride, acetyl bromide or ketene in an aprotic solvent such as toluene, hexane, THF, or dimethoxyethane with heating. Compound 21 is evaluated as having a weak, woody odor.

Treatment of unsaturated ketone 17 with a methyl organocuprate reagent such a lithium dimethylcuprate generated saturated ketone 22. Reduction of compound 22 with a suitable reducing agent such as lithium tri-sec-butylborohydride provided alcohol 23 as a mixture of two diastereoisomers with the depicted isomer as the principal component which has been determined to possess a woody odor.

Treatment of saturated ketone 19 with a methyl organometallic reagent such as methylmagnesium iodide, methylmagnesium chloride or methyllithium in an aprotic solvent such as toluene, hexane, THF, dimethoxyethane with heating yields the tertiary alcohol 24 which has been evaluated as having a woody odor.

TABLE 1

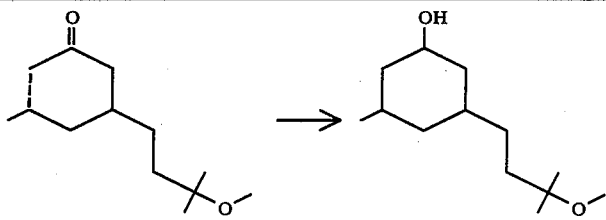

X - Dotted line is a carbon-carbon single bond
Y - Dotted line is a carbon-carbon double bond

| Starting Material | Conditions | Isomer Ratio | | | | (% Yield) |
| --- | --- | --- | --- | --- | --- | --- |
| | | A | B* | C | D | |
| X | Sodium borohydride, 2-propanol, room temperature. | — | 26.0 | 72.7 | 1.3 | (93) |
| X | Lithium aluminum hydride, tetrahydrofuran, 0° C. to room temperature. | 2.8 | 15.3 | 79.2 | 2.8 | (79) |
| Y | Raney nickel, hydrogen, 100 psi 100° C. | 4.7 | 22.6 | 65.4 | 7.4 | (90) |
| X | Sodium borohydride, acetone (2 equiv.), 2-propanol | — | 27.8 | 69.0 | 3.2 | |
| Y | Raney nickel, 2-propanol, hydrogen, room temperature | 8.6 | 21.8 | 62.3 | 8.3 | (78) |
| X | Lithium tri-t-butoxy-aluminum hydride, 0° C. to room temperature, tetrahydrofuran | — | 14.3 | 78.2 | 7.6 | (70) |
| X | Aluminum iso-propoxide, 2-propanol | — | 42.2 | 54.0 | 3.8 | (74) |
| X | Rhodium on carbon (5%), ethanol, hydrogen | — | 45.0 | 52.5 | 2.4 | |
| X | Lithium tri-sec-butyl-borohydride, −65° C., tetrahydrofuran | — | 87.3 | 5.5 | 4.6 | (86) |

*Diastereoisomer having the strongest woody, musky notes.

TABLE II
Structure and Odor Characteristics of Claimed Odorants

| Structure | Odor |
| --- | --- |
| 18 | woody, green |
| 20 | musky, sandalwood |
| 24 | warm, woody, |
| 23 | warm, woody |
| 29 | sandalwood |

Scheme IV: Formation of Monosubstituted Cyclohexanol

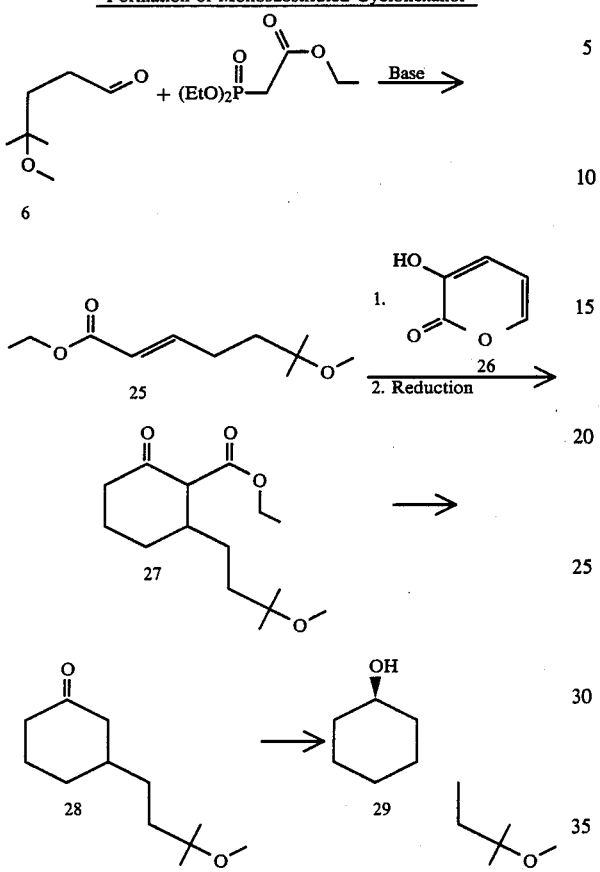

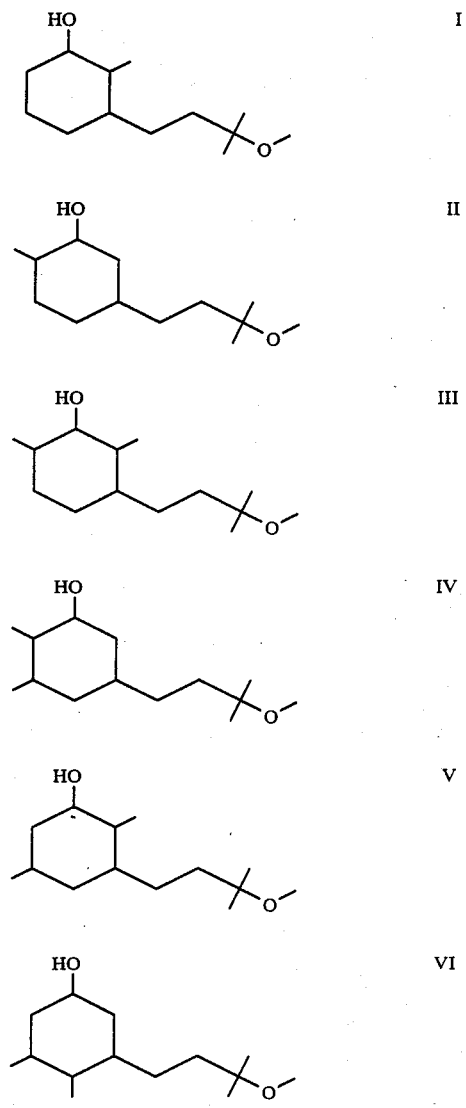

Scheme IV depicts the pathway to the monosubstituted cyclohexanol 29, the parent compound of the invention.

Aldehyde 6 is reacted with the anion of triethylphosphono acetate, generated by a suitable base such as methyllithium, sodium hydride, lithium hydride or phenyllithium in the temperature range of −20° to 20° C., to form the unsaturated ester 25.

The unsaturated ester 25 and 3-hydroxypyrone 26 are dissolved in a suitable solvent such as toluene, ethyl acetate, or hexane and heated in the temperature range of 15° to 25° C. for 3 to 16 hours. The resulting mixture is reduced using a suitable catalyst such as palladium on carbon, platinum on carbon, platinum oxide, Raney nickel or rhodium on carbon in an alcoholic solvent such as ethanol for 6 to 20 hours to yield the ketoester 27.

The ketoester 27 is decarboxylated to ketone 28 under aqueous basic conditions e.g. a hydroxide base such as sodium hydroxide, potassium hydroxide or barium hydroxide with a lower alcohol such as methanol or ethanol as a co-solvent at reflux.

Reduction of ketone 28 with a suitable reducing agent such as lithium aluminum hydride, sodium borohydride, diisobutylaluminum hydride, lithium tri-tert-butoxyaluminum hydride, or lithium borohydride, or hydrogenation catalysts such as palladium on carbon, Raney nickel or platinum oxide, yielded cyclohexanol 29 as a mixture of diastereoisomers. Lithium tri-sec-butylborohydride reduction yields the highest ratio of trans to cis diastereoisomers. This mixture of diastereomers was determined to possess warm, sandalwoody nuances.

Additional methylated analogues of the parent compound 29 which may exhibit desirable woody odors are as follows:

It is expected that the above compounds would possess a strong sandalwood odor. These compounds may be prepared from the aldehyde 6 shown below:

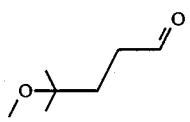

by methods known to those skilled in the art. For example, compounds I, II and III may be prepared by the alkylation of the ketone followed by reduction.

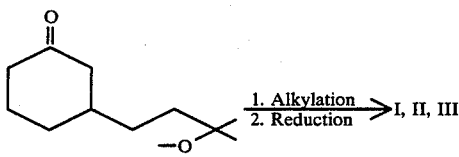

Similarly, compounds IV and V may be prepared by alkylation of the ketone followed by reduction.

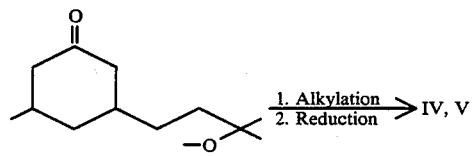

Using published methods (see B. A. McAndrew, *J. Soc. Cosmet. Chem.*, 28, pp. 629–639 (1977)), alcohol VI may be formed in the following manner

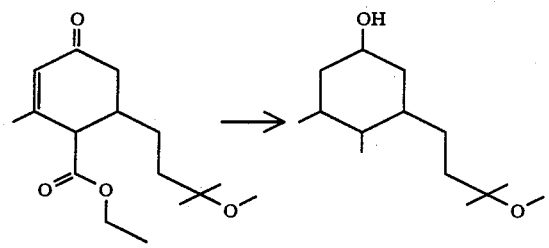

The following examples serve to illustrate the preparation of specific fragrance materials and their intermediates in accordance with the invention, but are not meant to limit the scope thereof.

The compounds of Examples 5, 6, 8, 9 and 19 may be employed in a number of consumable products where sandalwood aroma may be desirable, for example, colognes, detergent and soap compositions, liquid detergents, pre-fragranced coatings for textiles, among others.

The fragrance properties attributed to the compounds of Examples 5, 6, 8, 9 and 19 were determined by submitting each to a panel of expert perfumers. Their evaluations are included in each appropriate Example.

The fragrance compounds produced according to the invention are incorporated into colognes at concentrations of about 1.5% to 5.0% in 95% aqueous ethanol. The use of these compounds provides a cologne having a sandalwood character.

An air freshener produced from an accord containing compound 20 is mixed with ethanol and water to obtain a concentration range of 0.5% to 20% by weight to obtain a substantially homogeneous composition. The air freshener manifests a characteristic sandalwood fragrance.

The invention in its broader aspects is described with respect to the following examples which are intended only to illustrate the preferred embodiments of the invention and are not in any way intended to limit the scope thereof.

EXAMPLE 1

Preparation of 2,6-Dimethyl-2-methoxyhept-5-ene

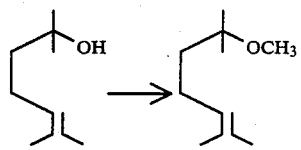

To sodium hydride (93.5 g, 3.9 mol) suspended in tetrahydrofuran (300 mL) was added 2,6-dimethylhept-5-en-2-ol (500 g, 3.5 mol) in tetrahydrofuran (1000 mL). The mixture was heated at reflux until gas evolution was complete. Dimethylsulfate (274 mL, 2.9 mol) in tetrahydrofuran (226 mL) was added to the cold (0° C.) mixture. After standing for 16 h, the mixture was heated at reflux for 7 hours. Aqueous workup yielded 2,6-dimethyl-2-methoxyhept-5-ene, bp$_{40}$ 65°–68° C. (461.5 g); NMR(CDCl$_3$)δ1.2(s,6H), 1.4–1.6(m,2H), 1.6(s,3H), 1.7(s,3H), 1.9–2.1(m,2H), 3.2(s,3H), 5.1–5.2(m,1H); IR(neat) 2970, 2932, 1462, 1442, 1373, 1357, 1195, 1072 cm$^{-1}$; MS(m/e) 41, 67, 73, 109, 124, 142.

EXAMPLE 2

Preparation of 4-Methoxy-4-methylpentanal

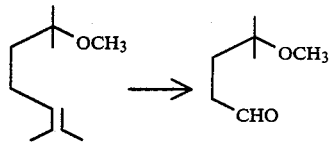

Method A

A stirred, cooled (−65° C.) mixture of 2,6-dimethyl-2-methoxyhept-5-ene (125 g, 1.25 mol), methylene chloride (500 mL) and methanol (500 mL) was treated with a gas stream enriched with ozone. Upon the appearance of a blue color pure oxygen was passed through the mixture followed by nitrogen. Dimethyl sulfide (88 mL, 1.4 mol) was added and the mixture was allowed to stand 16 hours at 25° C. Upon workup 4-methoxy-4-methylpentanal was obtained, bp$_{30}$ 85°–87° C. (64.4 g); NMR(CDCl$_3$)δ1.2(s,6H), 1.9(t,2H), 2.5(m,2H), 3.2(s,3H), 9.8(t,1H); IR(neat) 2975, 2825, 2725, 1730, 1470, 1370, 1090 cm$^{-1}$; MS(m/e) 43, 73, 83, 115.

Method B

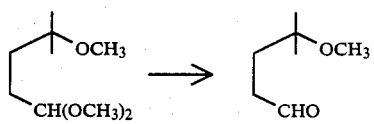

A mixture of 1,1,4-trimethoxy-4-methylpentane (3.2 g, 0.018 mol), tetrahydrofuran (100 mL), water (10 mL) and oxalic acid (1.0 g, 0.022 mol) was heated at reflux for 40 hours. Workup provided 4-methoxy-4-methylpentanal (2.0 g).

Method C

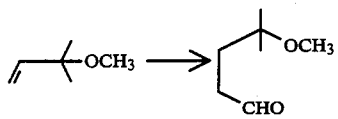

Dicobaltoctacarbonyl (1.6 g, 0.0047 mol), tri-n-butylphosphine (41.0 mL), 2-methoxy-2-methyl3-butene (30 g, 0.30 mol) and hexane (93 mL) were combined and placed under an atmosphere of 1:1 hydrogen:carbon monoxide and stirred at 195° C., pressure 1200 psi. The resulting mixture was distilled to yield 2.8 g 4-methoxy-4-methylpentanal.

EXAMPLE 3

Preparation of 3-(3-methoxy-3-methylbut-1-yl)-5-methylcyclohex-5-en-1-one

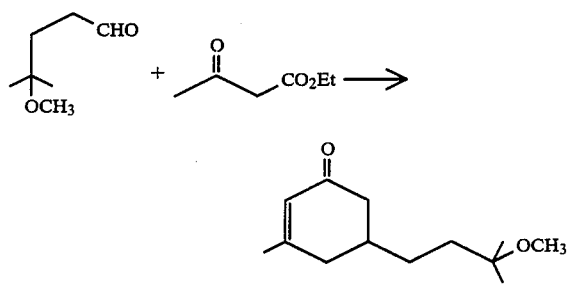

To a stirred mixture of 4-methoxy-4-methylpentanal (60 g, 0.46 mol) and ethyl acetoacetate (156 g, 1.2 mol) at 5° C. was added a 21% solution of piperidine in ethanol (4.1 mL). Further additions (4×18 mL) of the piperidine solution were made at about 24 hour intervals. The mixture was heated at reflux for 7 hours and concentrated to about 200 mL volume. Methanol (420 mL), water (420 mL) and sodium hydroxide (24 g) were added and the resulting mixture was heated at reflux 16 hours. Workup gave 3-(3-methoxy-3-methylbut-1-yl)-5-methylcyclohex-5-en-1-one bp$_{0.1}$ 135°–140° C. (69.2 g); NMR(CDCl$_3$)δ1.2(s,6H), 0.9–1.6(m,5H), 1.9(s,3H), 5.9(brs,1H); IR(neat) 2975, 2930, 1675, 1640, 1380, 1080 cm$^{-1}$; MS(m/e) 43, 73, 81, 109, 122, 163, 196.

EXAMPLE 4

Preparation of 3-(3-Methoxy-3-methylbut-1-yl)-5-methylcyclohexan-1-one

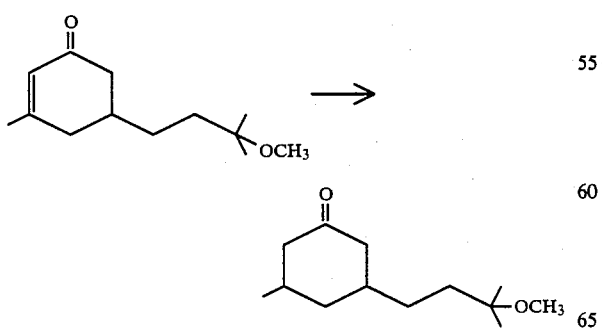

A solution of 3-(3-methoxy-3-methylbut-1-yl)-5-methylcyclohex-5-en-1-one (30.0 g, 0.14 mol) in methanol (150 mL) was placed in a thick walled bottle. Palladium on charcoal (5%, 2.0 g) was added and the mixture was shaken under 53.5 psi of hydrogen. When the theoretical amount of hydrogen had been consumed, workup yielded 3-(3-methoxy-3-methylbut-1-yl)-5-methylcyclohexan-1-one as a mixture of two diastereoisomers bp$_{0.5}$ 104°–107° C. (27.6 g, ratio 69:93.1); NMR(CDCl$_3$)δ1.0(d,3H), 1.1(s,6H), 1.3–1.5(m,6H), 1.6–2.0(m,4H), 2.2–2.4(m,2H),3.1(s,3H). IR(neat) 2970, 2925, 1720, 1360, 1090 cm$^{-1}$; MS(m/e) 41, 73, 124, 147, 165, 180, 197.

EXAMPLE 5

Preparation of 3-(3-Methoxy-3-methylbut-1-yl)-5-methylcyclohex-5-en-1-ol

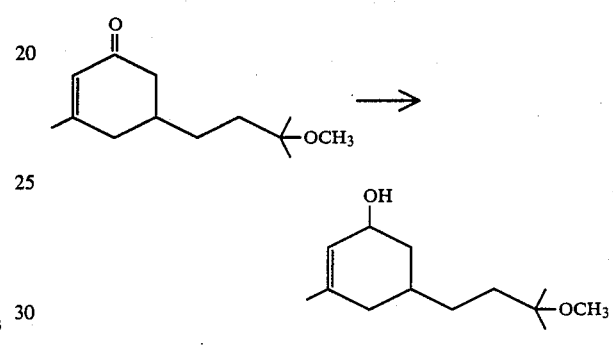

To a suspension of lithium aluminum hydride (0.1 g, 0.0024 mol) in tetrahydrofuran (5 mL) cooled to 0° C. was added 3-(3-methoxy-3-methylbut-1-yl)-5-methylcyclohex-5-en-1-one (1.0 g, 0.0048 mol) in tetrahydrofuran (5 mL). The mixture warmed on standing 16 hours and was treated with 10% sodium hydroxide solution. Subsequent workup yielded 3-(3-methoxy-3-methylbut-1-yl)-5-methylcyclohex-5-en-1-ol as a mixture of two diastereoisomers (ratio: 6.5:93.5, 0.853 g). This material was determined to possess green, woody notes. NMR(CDCl$_3$)δ0.8–1.1(m,2H), 1.2(s,6H), 1.3–1.6(m,5H), 1.7(s,1H), 1.9–2.2(m,5H), 3.2(s,3H), 4.2(brs,1H), 5.4(s,1H); IR(neat) 3400, 2975, 2925, 1670, 1380, 1360, 1090 cm$^{-1}$; MS(m/e) 43, 73, 91, 106, 124, 147, 162, 180, 194.

EXAMPLE 6

Preparation of 3-(3-Methoxy-3-methylbut-1-yl)-5-methylcyclohexan-1-ol

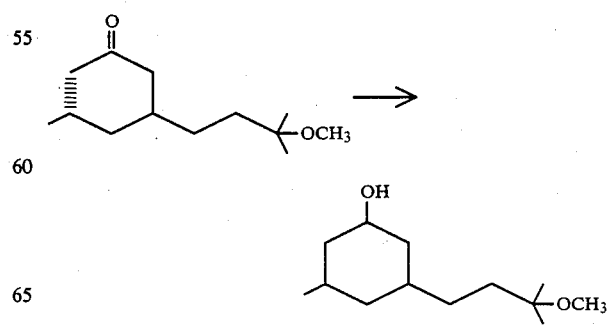

Method A

A solution of lithium tri-sec-butylborohydride (267 mL of a 1M solution in tetrahydrofuran, 0.27 mol) was added to a cooled (−65° C.) solution of 3-(3-methoxy-3-methylbut-1-yl)-5-methylcyclohexan-1-one (48.6 g, 0.22 mol) dissolved in tetrahydrofuran (350 mL). The solution was stirred at 25° C. for 16 hours and was quenched by addition of sodium hydroxide (10% aqueous, 165 mL) followed by hydrogen peroxide (30% aqueous, 170 mL). Workup yielded 3-(3-methoxy-3-methylbutyl)-5-methyl cyclohexan-1-ol as a mixture of diastereoisomers (ratio 90.1:7.2:2.7), bp$_{0.75}$ 120°–122° C. (40.7 g). This compound and mixtures of diastereomers possess strong, tenacious, sandalwoody, musky notes. NMR(CDCl$_3$)δ0.6 (q,1H), 0.9(d,3H), 1.0–1.1(m,2H), 1.1(s,6H), 1.2–1.3 (m,2H), 1.4–1.6(m,2H), 1.6–1.9(m,5H), 2.2(brs,1H), 3.2(s,3H), 4.1(m,1H). IR(neat) 3400, 2975, 2925, 1460, 1385, 1365, 1210, 1090, 1015 cm$^{-1}$; MS(m/e) 43, 73, 93, 111, 149, 167, 182, 199, 200.

Method B

A mixture of 3-(3-methoxy-3-methylbut-1-yl)-5-methylcyclohex-5-en-1-one (1.0 g, 0.0048 mol) in 2-propanol (40 mL) and Raney nickel (about 0.1 g) was shaken under hydrogen (37 psi) at 25° C. for 16 hours. Subsequent workup yielded 3-(3-methoxy-3-methylbut-1-yl)-5-methylcyclohexan-1-ol (0.78 g) as a mixture of four diastereoisomers (ratio 8.1:20.6:57.8:7.8).

Method C

A solution of 3-(3-methoxy-3-methylbut-1-yl)-5-methylcyclohexan-1-one (0.50 g, 0.0024 mol) in tetrahydrofuran (1 mL) was added to a suspension of lithium aluminum hydride (0.10 g, 0.0027 mol) in tetrahydrofuran (1 mL) cooled to 0° C. The mixture was stirred at 20° C. for 16 h. Subsequent workup yielded 3-(3-methoxy-3-methylbutyl)-5-methylcyclohexanol (0.40 g) as a mixture of four diastereoisomers (ratio 2.8:15.3:79.2:2.8).

EXAMPLE 7

Preparation of 3-(3-Methoxy-3-methylbut-1-yl)-5,5-dimethylcyclohexan-1-one

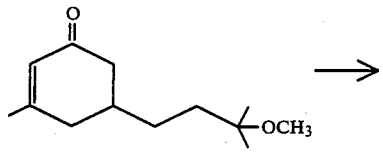

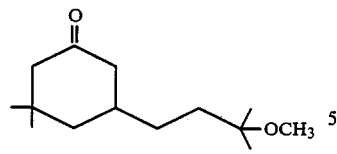

To a suspension of copper(I) iodide (6.0 g, 0.032 mol) in tetrahydrofuran (120 mL) cooled to 0° C. was added a methyllithium solution (45 mL of a 1.4M solution in diethyl ether, 0.063 mol). After stirring 0.5 hour, 3-(3-methoxy-3-methylbutyl)-5-methylcyclohex-5-en-1-one (2.0 g, 0.0095 mol) in tetrahydrofuran (80 mL) was slowly added. After stirring 2.5 hours, the mixture was added to ice cold dilute hydrochloric acid. Subsequent workup yielded 3-(3-methoxy-3-methylbutyl)-5,5-dimethylcyclohexan-1-one, bp$_{0.5}$ 125°–130° C. (1.3 g); NMR (CDCl$_3$)δ0.9(s,3H), 1.1(s,3H), 1.1(s,6H), 1.2–1.6(m,6H), 1.6–2.5(m,5H), 3.2(s,3H); IR(neat) 2960, 1715, 1365, 1085 cm$^{-1}$. MS(m/e) 41, 55, 73, 138, 161, 211, 212.

EXAMPLE 8

Preparation of 3-(3-Methoxy-3-methylbut-1-yl)-5,5-dimethylcyclohexan-1-ol

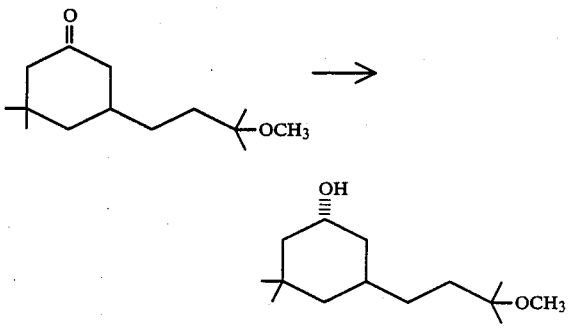

To lithium tri-sec-butylborohydride (2.7 mL of a 1.0M solution in tetrahydrofuran, 0.0027 mol) cooled to −65° C. was added 3-(3-methoxy-3-methylbutyl)-5,5-dimethylcyclohexan-1-one (0.5 g, 0.0022 mol) dissolved in tetrahydrofuran (3.5 mL). The mixture was allowed to stir at 25° C. for 16 hours. Workup yielded 3-(3-methoxy-3-methylbut-1-yl)-5,5-dimethylcyclohexan-1-ol, bp$_{1.0}$ 210°–212° C. (0.31 g). This compound was determined to possess a warm woody note. NMR(CDCl$_3$)δ0.9(s,3H), 1.1 (s,3H), 1.2(s,6H), 1.2–1.4(m,4H), 1.4–1.7(m,6H), 1.7–1.9(m,2H), 3.2(s,3H), 4.2(m,1H); IR(neat) 3425, 2970, 2940, 1470, 1365, 1080 cm$^{-1}$; MS(m/e) 43, 55, 73, 125, 163, 213, 214.

EXAMPLE 9

Preparation of 3-(3-methoxy-3-methylbutyl)-1,5-dimethylcylohexan-1-ol

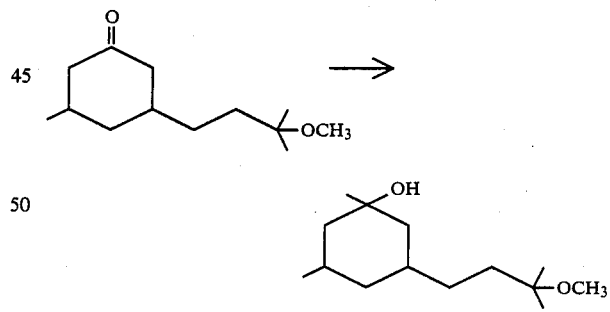

3-(3-Methoxy-3-methylbut-1-yl)-5-methylcyclohexan-1-one (5.0 g, 0.025 mol) dissolved in diethyl ether (5.0 mL) was added to a cooled (5° C.) solution of methylmagensium iodide formed by treating magnesium turnings (0.70 g, 0.028 mol) in diethyl ether (20 mL) with iodomethane (1.6 mL, 0.026 mol). After stirring 16 hours at 25° C., a saturated aqueous ammonium chloride solution (ca. 2 mL) was added and subsequent workup yielded 3-(3-methoxy-3-methylbutyl)-1,5-dimethylcyclohexan-1-ol as a mixture of diastereoisomers in a ratio of 2.9:65.6:1.9:29.6, bp$_{0.5}$ 147°–149° C. This compound was determined to possess a warm woody note. NMR(CDCl$_3$)δ0.5(m,1H), 0.9(d,3H), 1.0–1.1(m,1H), 1.2(s,6H), 1.3(s,3H), 1.3–1.9(m,10H), 1.9–2.0(brs,1H), 3.2(s,3H); IR(neat) 3400, 2925, 1460, 1370, 1220, 1080 cm$^{-1}$; MS(m/e) 43, 55, 73, 107, 122, 163, 181, 213, 214.

EXAMPLE 10

Preparation of 2-Methoxy-2-methylhex-5-ene

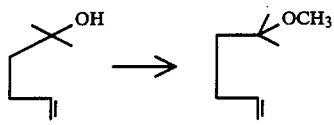

To a stirred suspension of sodium hydride (46.8 g of a 60% oil dispersion, 1.15 mol) in tetrahydrofuran (240 mL) was added 2-methylhex-5-en-2-ol (120 g, 1.05 mol) in tetrahydrofuran (240 mL). Dimethylsulfate (75 mL, 0.79 mol) in tetrahydrofuran (120 mL) was added to the cooled (0° C.) mixture. The mixture was heated at reflux for 6 hours. Workup yielded 2-methoxy-2-methylhex-5-ene, bp$_{40}$ 53°–58° C. (51.36 g); NMR(CDCl$_3$)δ1.1(s,6H), 1.5–1.6(m,2H), 2.0–2.2(m,2H), 3.2(s,3H), 4.8–5.1(m,2H), 5.7–6.0(m,1H); IR(neat) 2960, 2925, 1640, 1460, 1360, 1300, 1085 cm$^{-1}$; MS(m/e) 43, 55, 73, 81, 95, 97, 113, 114.

EXAMPLE 11

Preparation of 4-Methylpent-4-enal

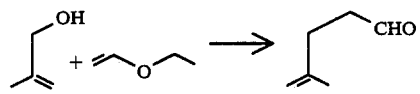

Methallyl alcohol (15 g, 0.21 mol), ethyl vinyl ether (120 mL, 1.26 mol) and mercuric acetate (4.2 g, 0.013 mol) were combined and heated at 200° C. in a sealed container for 2 h. Distillation yielded 4-methylpent-4-enal, bp 110°–112° C. (14.5 g); NMR(CDCl$_3$)δ1.8(s,3H), 2.3(m,2H), 2.6(m,2H), 5.7(brs,2H), 9.8(t,1H); IR(neat) 2950, 2900, 2700, 1725, 1650, 1440, 1370, 885 cm$^{-1}$; MS(m/e) 41, 55, 56, 70, 83, 98, 115.

EXAMPLE 12

Preparation of 2-Methylhex-5-en-2-ol

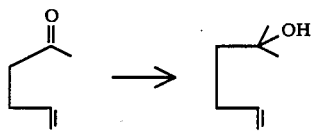

Methyllithium (800 mL of a 1.4M solution of diethyl ether, 1.1 mol) was added to mixture of hex-5-en-2-one (100 g, 1.0 mol) in tetrahydrofuran (800 mL) cooled to −78° C. The mixture was allowed to warm to 25° C. over the course of 1 hour, after which saturated aqueous ammonium chloride solution was added. Workup yielded 2-methylhex-5-en-2-ol, bp$_{30}$ 63°–66° C. (140 g); NMR(CDCl$_3$)δ1.2(s,6H), 1.5–1.6(m,2H), 2.1–2.2(m,2H), 2.5(s,1H), 4.9–5.1(m,2H), 5.7–5.9(m,1H); IR(neat) 3350, 2945, 2905, 1635, 1370, 1140, 985, 900 cm$^{-1}$; MS(m/e) 43, 58, 81, 99, 114.

EXAMPLE 13

Preparation of 1,1,4-Trimethoxy-4-methylpentane

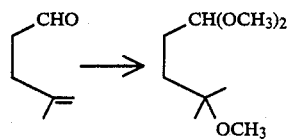

Method A:

A mixture of methanol (30 mL), Dowex 50 acidic resin (1.0 g) and 4-methylpent-4-enal (3.9 g, 0.0031 mol) was heated at reflux for 16 h. Workup yielded 1,1,4-trimethoxy-4-methylpentane, bp$_{125}$ 86°–88° C. (3.3 g). NMR(CDCl$_3$)δ1.2(s,6H), 1.5–1.8(m,4H), 3.2(s,3H), 3.3(s,6H), 4.4(t,1H). IR(neat) 2975, 2930, 1470, 1385, 1365, 1160, 1090, 1055 cm$^{-1}$. MS(m/e) 43, 55, 73, 81, 83, 97, 115.

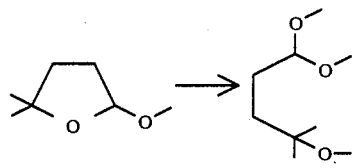

Method B:

A mixture of 2-methoxy-5,5-dimethyltetrahydrofuran (10 g, 0.077 mol), methanol (7.9 g, 0.25 mol), concentrated sulfuric acid (1.0 mL), Montmorillonite clay (1.0 g) and trimethyl orthoformate (29 g, 0.27 mol) was heated at reflux 16 hours. After cooling the mixture was filtered and diluted with water and 10% NaOH (aq.) and extracted with hexanes. The extracts were dried (sodium sulfate) and distilled to yield the desired product, 9.0 g.

The above procedure may also be carried out on the other products of the hydroformylation of 3-methylbut-1-en-3-ol such as the dimeric ether and the enol ether shown below.

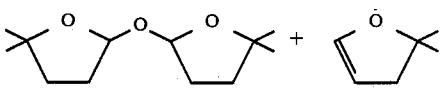

EXAMPLE 14

Preparation of 1-Acetoxy-3-(3-methoxy-3-methylbut-1-yl)-5-methylcyclhexane

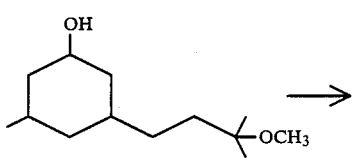

-continued

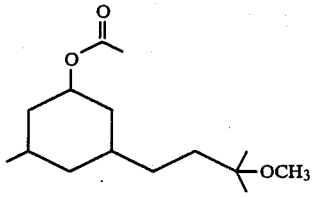

Acetic anhydride (1.4 mL, 0.014 mol), 3-(3-methoxy-3-methylbut-1-yl)-5-methylcyclohexan-1-ol (2.0 g, 0.0093 mol), toluene (3.0 mL) and sodium acetate (0.05 g) were combined and heated at reflux for 16 hours. Workup provided 1-acetoxy-3-(3-methoxy-3-methylbut-1-yl)-5-methylcyclohexane, bp$_{0.5}$ 175°–177° C. (1.61 g) as a mixture of diasteroisomers (ratio 92.3:3.2:4.5); NMR(CDCl$_3$)δ0.6(q,1H), 0.9(d,3H), 1.0–1.3(m,3H), 1.2(s,6H), 1.4–1.6(m,4H), 1.6–2.0(m,4H), 2.1(s,3H), 3.2(s,3H), 5.1(m,1H); IR(neat) 2960, 2925, 1740, 1460, 1380, 1250, 1085, 1015 cm$^{-1}$; MS(m/e) 43, 73, 93, 108, 149, 164, 181, 241, 242.

EXAMPLE 15

Preparation of 2,6-Dimethylhept-5-en-2-ol

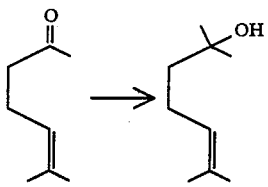

To a cooled (0° C.) solution of methylmagnesium chloride formed by exhaustive treatment of magnesium turnings (121.5 g, 5.0 mol) in tetrahydrofuran (1500 mL) with chloromethane was added with stirring 6-methyl-hept-5-en-2-one (600 g, 4.8 mol) in tetrahydrofuran (1500 mL). Stirring was continued for 16 hours at 25° C. After treatment with saturated aqueous ammonium chloride solution (about 200 mL) workup yielded 2,6-dimethylhept-5-en-2-ol, bp$_{40}$ 83°–85° C., (538 g); NMR (CDCl$_3$)δ1.2(s,6H), 1.3–1.5(m,2H), 1.8(s,3H), 1.9(s,3H), 2.1(m,2H), 2.9(s,1H), 5.3(m,1H); IR(neat) 3375, 2975, 2940, 1470, 1450, 1385, 1200, 1155, 1135, 930, 910 cm$^{-1}$. MS(m/e) 41, 59, 69, 81, 109, 124, 142.

EXAMPLE 16

Preparation of Ethyl 6-methoxy-6-methoxy 6-methyl-2-heptenoate

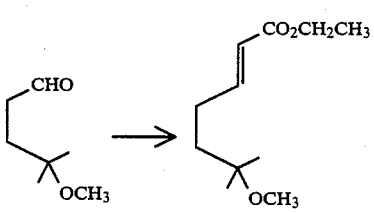

Sodium hydride (5.5 g, 0.27 mol) was suspended in tetrahydrofuran (95 mL) under a nitrogen atmosphere. A solution of triethylphosphonoacetate (57 g, 0.25 mol) in tetrahydrofuran (95 mL) was added dropwise to the suspension with stirring at 29° C. The mixture was cooled to 5° C. and 4-methoxy-4-methylpentanal (30 g, 0.23 mol) in tetrahydrofuran (75 mL) was added in a single portion. After 2 hours the mixture was added to water and extracted with diethyl ether. The extracts were dried (MgSO$_4$) and concentrated to an oil which was distilled, bp$_{0.5}$ 95°–97° C. (34.8 g); NMR(CDCl$_3$)δ1.2(s,6H), 1.3(t,3H), 1.6(m,2H), 2.3(m,2H), 3.2(s,3H), 4.2(q,2H), 5.8(d,1H), 7.0(m,1H); IR(neat) 2975, 2940, 2820, 1730, 1660, 1365, 1265, 1220, 1180, 1135, 1080 cm$^{-1}$; MS(m/e) 43, 55, 73, 95, 123, 139, 155, 185, 187.

EXAMPLE 17

Preparation of 2-Carbethoxy-3-(3-methoxy-3-methylbut-1-yl)cyclohexanone

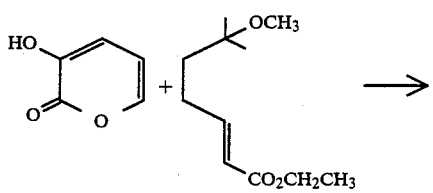

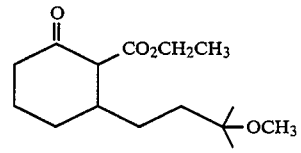

A mixture of 3-Hydroxypyrone (obtained by the procedure of R. H. Wiley and C. H. Jorboe, *J. Am. Chem. Soc.*, 78, 2398, (1956), 5.0 g, 0.045 mol) and ethyl 6-methoxy-6-methyl-2-heptenoate (8.9 g, 0.045 mol) were dissolved in toluene (15 mL) and heated in a sealed vessel for 7 hours at 200° C. After cooling 5% Pd/C (1.0 g) and methanol (50 mL) were added and the vessel was pressurized with hydrogen gas (200 psi). After stirring 20 hours the mixture was filtered and concentrated to the residue. The crude product decomposed on distillation. No further purification was attempted. NMR of crude material (CDCl$_3$)δ1.2(s,6H), 1.3(t,3H), 3.2(s,3H), 3.7(m,1H), 4.2(m,2H); IR(neat) 2600–3800, (broad band), 2990, 2950, 1740, 1720, 1680, 1650, 1620, 1470, 1390, 1370, 1220, 1090 cm$^{-1}$.

EXAMPLE 18

Preparation of 3-(3-Methoxy-3-methylbut-1-yl)cyclohexanone

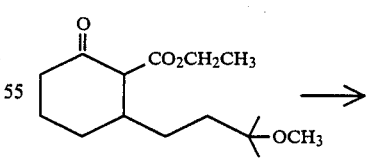

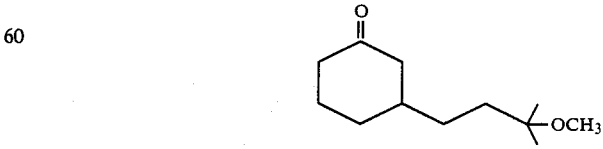

Crude 2-carbethoxy-3-(3-methoxy-3-methylbut-1-yl)cyclohexanone (7.0 g) of example 17 was added to a mixture of potassium hydroxide (3.0 g), methanol (50 mL) and water (50 mL) and heated at reflux 4.5 hours. The cooled mixture was extracted with hexane, the extracts were dried (Na₂SO₄) and concentrated to an oil which was purified by bulb to bulb distillation, airbath temperature 175° C., 0.1 mm Hg to yield 3-(3-methoxy-3-methylbut-1-yl)cyclohexanone (1.0 g); NMR(CDCl₃)δ1.2(s,6H), 1.2–1.5(m,5H), 1.6–1.8(m,2H), 1.9–2.1(m,3H), 2.2–2.4(m,3H), 3.2(s,3H); IR(neat) 2970, 2950, 1720, 1460, 1370, 1230, 1090 cm⁻¹; MS(m/e) 41, 55, 73, 110, 133, 151, 183, 184.

EXAMPLE 19

Preparation of 3-(3-Methoxy-3-methylbut-1-yl)cyclohexanol

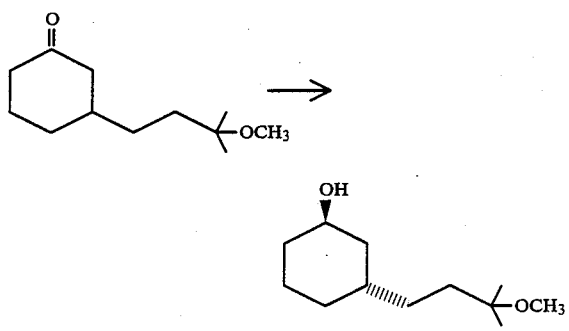

3-(3-methoxy-3-methylbut-1-yl)cyclohexanone (1.4 g, 0.0051 mol) was dissolved in tetrahydrofuran (10 mL) and cooled to −78° C. under a nitrogen atmosphere with stirring. A solution of lithium tri-sec-butylborohydride (6.1 mL of a 1M solution of tetrahydrofuran, 0.0061 mol) was added. The mixture was allowed to come to 20° C. over 16 hours and 10% NaOH (aq, 4.0 mL) was added, followed by 30% hydrogen peroxide (aq, 4.0 mL). The mixture was extracted with hexane. The extracts were dried (Na₂SO₄) and concentrated to the residue which was purified by bulb to bulb distillation (air bath temp 175° C., 0.1 mm Hg) to yield 3-(3-methoxy-methylbut-1-yl)cyclohexanol as a mixture of diastereoisomers in the ratio of 94:6 (0.7 g). NMR(CDCl₃)δ1.1(s,6H), 1.2–1.8(m,13H), 3.2(s,3H), 4.1(brs,1H). IR(neat) 3410, 2990, 2960, 2870, 1460, 1370, 1110, 1090, 980 cm⁻¹. MS(m/e) 43, 73, 109, 124, 143, 181, 201, 214.

EXAMPLE 20

FLORAL BOUQUET FORMULATION

A floral bouquet composition was prepared using the following formulation:

| Material | % |
|---|---|
| Oil Lemon Rectified | 1.0 |
| Linalool FCC Synthetic | 2.0 |
| Phenylethyl Alcohol FCC | 11.0 |
| Benzyl Acetate FCC Extra | 1.5 |
| Styrolyl Alcohol | 1.5 |
| Citronellol R BASF | 5.5 |
| Hydroxycitonellal FCC Extra | 4.0 |
| Eugenol FCC extra | 0.5 |
| Lillial | 1.0 |
| Hedione | 2.0 |
| Lyral | 1.5 |
| Hexyl cinnamic aldehyde FCC | 2.0 |
| Benzyl salicylate | 5.5 |
| Methyl ionone gamma pure | 3.0 |
| Musk ether | 2.0 |
| Aldehyde C-12 FCC lauric | 0.1 |
| Diethyl phthalate | 45.9 |
| 3-(3-methoxy-3-methylbut-1-yl)-5-methylcyclohexanol of Example 6 | 10.00 |
| | 100.00 |

EXAMPLE 21

WOODY PERFUME FORMULATION

A woody perfume composition was prepared by mixing the following formulation:

| Material | % |
|---|---|
| Heliotropin extra FCC | 1.0 |
| Musk ether | 2.5 |
| Coumarin | 7.0 |
| Benzyl acetate FCC extra | 10.0 |
| Hydroxycitronellal FCC extra | 3.0 |
| Terpinyl acetate FCC | 2.0 |
| Oil Bergamot Rectified | 10.0 |
| Methyl Ionone Gamma Pure | 5.0 |
| Cedrol Recrystallized | 5.0 |
| Oil Cedarwood Terpeneless | 3.0 |
| Cedryl Acetate | 4.0 |
| Oil Amyris FCC | 12.0 |
| Dipropylene Glycol | 25.5 |
| 3-(3-methoxy-3-methylbut-1-yl)-5-methylcyclohexanol of Example 6 | 10.0 |
| | 100.00 |

EXAMPLE 22

FLORAL AIR FRESHNER FORMULATION

A floral composition was prepared using the following formulation:

| Material | % |
|---|---|
| Oil Lemon Rectified | 1.0 |
| Linalool FCC Synthetic | 2.0 |
| Phenylethyl Alcohol FCC | 11.0 |
| Benzyl Acetate FCC Extra | 1.5 |
| Styrolyl Alcohol | 1.5 |
| Citronellol R BASF | 5.5 |
| Hydroxycitonellal FCC Extra | 4.0 |
| Eugenol FCC Extra | 0.5 |
| Lillial | 1.0 |
| Hedione | 2.0 |
| Lyral | 1.5 |
| Hexyl Cinnamic Aldehyde FCC | 2.0 |
| Benzyl Salicylate | 5.5 |
| Methyl Ionone Gamma Pure | 3.0 |
| Musk ether | 2.0 |
| Aldehyde C-12 FCC Lauric | 0.1 |
| Diethyl Phthalate | 45.9 |
| 3-(3-methoxy-methylbut-1-yl)-5-methylcyclohexanol of Example 6 | 10.00 |
| | 100.00 |

The above formulation was diluted to 5% concentration with 95% Ethanol and distilled water was added with stirring until the solution turned cloudy. The mixture was backtitrated to clarity with more 95% Ethanol. This was used in a wick-type room air freshner.

EXAMPLE 23

Chypre Formulation
A chypre fragrance composition was
prepared using the following formulation:

| Material | % |
|---|---|
| Oil Bergamot | 26.0 |
| Oil Orange Sweet | 13.0 |
| Methyl Ionone | 20.0 |
| Oil Rose | 2.0 |
| Jasmine Absolute | 5.0 |
| Oil Basil Sweet | 0.5 |
| Oil Estragon | 0.5 |
| Benzyl Salicylate | 0.3 |
| Oil Ylang Extra | 0.3 |
| Cinnamic Alcohol | 0.6 |
| Eugenol | 1.8 |
| Aldehyde C-14 | 0.3 |
| 10% Sol. Aldehyde C-12 NMA in DEP Odorless | 0.2 |
| 10% Sol. Aldehyde C-11 Undecylenic in Phthalate Odorless | 1.0 |
| Civet Absolute | 1.0 |
| Coumarin | 4.0 |
| Labdanum Resinoid | 3.5 |
| Musk Ketone | 3.0 |
| Oakmoss Absolute | 3.5 |
| Oil Patchouly | 3.5 |
| Vanillin | 0.5 |
| Oil Vetiver Reunion | 5.5 |
| 3-(3-Methoxy-3-methylbut-1-yl)cyclohexanol of Example 19 | 10.0 |
| | 100.0 |

EXAMPLE 24

Preparation of Sandalwood Base
A sandalwood fragrance base was
prepared using the following formulation:

| Material | % |
|---|---|
| Oil Balsam Gurgon | 2.0 |
| Oil Amyris | 8.0 |
| Osyrol BBA | 10.0 |
| 3-(3-methoxy-3-methylbut-1-yl)cyclohexanol of Example 19 | 80.0 |
| | 100.0 |

What is claimed is:

1. A compound having the structure

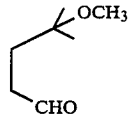

* * * * *